United States Patent
Mikami et al.

[11] Patent Number: 5,814,220
[45] Date of Patent: Sep. 29, 1998

[54] PROCESS FOR PRODUCING BLOOD SEPARATING AGENT

[75] Inventors: Hiroshi Mikami, Kanagawa; Kenshin Nakahara, Okayama; Mariko Kimura, Kanagawa; Toshikazu Ishii, Tokyo, all of Japan

[73] Assignee: Mitsubishi Chemical Corporation, Tokyo, Japan

[21] Appl. No.: 763,755

[22] Filed: Dec. 11, 1996

[30] Foreign Application Priority Data

Dec. 20, 1995 [JP] Japan ................................. 7-348586

[51] Int. Cl.$^6$ ............................ B01J 13/00; B01D 17/00
[52] U.S. Cl. ...................... 210/516; 210/518; 252/315.2; 252/315.5; 252/315.6
[58] Field of Search ..................... 210/516, 518, 210/789; 435/2; 252/60, 315.2, 315.01, 315.5, 315.6

[56] References Cited

U.S. PATENT DOCUMENTS

| | | | |
|---|---|---|---|
| 3,852,194 | 12/1974 | Zine, Jr. ................................ | 210/789 |
| 4,310,430 | 1/1982 | Ichikawa et al. ..................... | 210/782 |
| 4,664,842 | 5/1987 | Knudson, Jr. et al. ............... | 252/315.2 |
| 4,770,779 | 9/1988 | Ichikawa et al. ..................... | 210/516 |
| 5,160,454 | 11/1992 | Knudson, Jr. et al. ............... | 252/315.2 |
| 5,364,632 | 11/1994 | Benita et al. ......................... | 424/450 |
| 5,449,712 | 9/1995 | Gierke et al. ......................... | 427/377 |

FOREIGN PATENT DOCUMENTS

| | | |
|---|---|---|
| 0375566 | 6/1990 | European Pat. Off. . |
| 1372701 | 11/1974 | United Kingdom . |

Primary Examiner—John Kim
Attorney, Agent, or Firm—Dilworth & Barrese

[57] ABSTRACT

A process for the production of a blood separating agent is disclosed which comprises supplying a mixture solution containing (a) a separation layer forming high molecular weight compound as the main component and (b) a thixotropy-providing agent selected from the group consisting of inorganic fine particles and organic gelling agents into a cylinder block of a homogenizer having the cylinder block equipped with a plunger capable of performing reciprocating movement and a valve body which is connected thereto and equipped with a valve member, a valve sheet and an impact ring, and applying a compressive shearing stress to the mixture in said homogenizer at such a temperature that viscosity of the solution becomes $1 \times 10^4$ centipoises or less, thereby obtaining a blood separating agent in the form of a dispersion or a uniform gel. A blood separating agent having excellent storage stability can be obtained with improved productivity per unit time.

8 Claims, 5 Drawing Sheets

PROCESS FOR PRODUCING BLOOD SEPARATING AGENT

FIELD OF THE INVENTION

This invention relates to a process for the production of a blood separating agent having high storage stability.

BACKGROUND OF THE INVENTION

Blood separating agents are used by placing them on the bottom of vacuum blood-collecting tubes to be used in blood tests. The blood-collecting tubes, after injection of blood therein, are subjected to centrifugation to separate the blood sample into a serum portion and a clot portion or a plasma portion and a hematocyte portion making use of the difference in their specific gravities. In this stage, the blood separating agent provides an intermediate specific gravity of the two components to form a separating layer between these components, thereby facilitating separation of these two components.

As the separating agent to be used in the blood separation, those in which a separation layer-forming high molecular weight compound (a) such as silicone oil, chlorinated polybutene, polyisobutene, an acrylic polymer, a copolymer of α-olefin having 6 to 20 carbon atoms with dimethyl maleate, a styrene-dimethyl maleate copolymer or the like is used as the main component and blended with a thixotropy providing agent (b) have been known and put into practical use (JP-A-56-40451, JP-A-56-166956, JP-A-57-1457, JP-A-58-37560, JP-A-62-197765, JP-A-62-198759, JP-A-62-199644, JP-A-2-168159, JP-A-5-203640, JP-A-6-148174, JP-A-61-48175, JP-A-6-220132, JP-A-6-220135, JP-A-6-220136, JP-A-62-22056, JP-A-6-324034 and JP-A-7-27760; the term "JP-A" as used herein means an "unexamined published Japanese patent application").

As the thixotropy providing agent, those which are used in adjusting specific gravity and viscosity are known, which include inorganic fine particles such as those of silica, clay, and the like, and organic gelling agents such as a condensation product of sorbitol with benzaldehyde (dibenzylidene sorbitol), hydrogenated castor oil, 12-hydroxystearic acid, a nitrohumic acid addition product of water soluble protein, glutamic acid amide, a dimethanol-octahydronaphthalene copolymer, and the like.

The aforementioned separation layer-forming high molecular compound is hydrophobic, and the inorganic fine particles and organic gelling agent provide a viscosity increasing effect and thixotropic property.

In the industrial scale production of the blood separating agent, a separation layer forming high molecular weight compound (a) and an inorganic compound (b) are subjected to stirring, mixing and gelation, using a three roller system, over an extended period of time while applying a shearing force (JP-A-5-10945, JP-A-5-80044, JP-A-6-148174, JP-A-6-148175, JP-A-6-220135 and JP-A-7-27760).

On the laboratory scale, the blood separating agent has been produced by adding an inorganic gelling agent (b) to a separation layer forming high molecular weight compound (a) in a flask, stirring the mixture for an extended period of time while heating at 100° to 200° C. and then cooling it to room temperature, thereby providing a thixotropic property (JP-A-61-39736 and JP-A-2-168159).

In the former method in which a three roller system (field roller, center roller and apron roller) is employed, a mixture composed of a separation layer forming high molecular weight compound (a) and inorganic fine particles (b) as a gelling agent is supplied into the gap between the field roller and center roller and compressed with the rollers by rotating them at different rates (the latter having a higher rotation rate) to create shearing force and thereby increase the viscosity of the mixture, and the thus thickened blood separating agent is recovered with a stroking knife at the rear part of the apron roller.

Since the three roller system method is suitable for the treatment of a kneaded mixture having a high viscosity, it has advantages in that gelation can be effected at ambient temperature and cleaning can be accompanied easily, but has the following three disadvantages:

(1) The quantity able to be processed is small in comparison to the size of the apparatus;

(2) Additional devices are required to automate charging of the high viscosity materials and discharging of the product blood separating agent; and (3) Being an open system apparatus, it is apt to cause contamination by dust, dirt and like foreign materials entering the product blood separating agent.

On the other hand, the latter method in which heating, stirring and cooling are carried out in a flask can be applied to organic gelling agents but cannot be used when inorganic fine particles are used as the gelling agent. In addition, such method results in a low level of production.

SUMMARY OF THE INVENTION

In view of the above, it therefore becomes an object of the present invention to provide a process for the production of a blood separating agent, which can produce an agent having substantially the same performance as the prior art agents, is unlikely to cause contamination of foreign materials in comparison with the prior art methods and can increase the production quantity per unit time sharply in comparison with the three-roller system method.

Accordingly, the present invention provides a process for the production of a blood separating agent, which comprises supplying a mixture containing (a) a separation layer forming high molecular weight compound as the main component and (b) a thixotropy providing agent selected from the group consisting of inorganic fine particles and organic gelling agents to a cylinder block of a homogenizer having the cylinder block equipped with a plunger capable of performing reciprocating movement and a valve body which is connected thereto and equipped with a valve member, a valve sheet and an impact ring, and applying a compressive shearing stress to the mixture in the homogenizer at such a temperature that viscosity of the mixture becomes $1 \times 10^4$ centipoises or less, thereby obtaining a blood separating agent in the form of a dispersion or a uniform gel.

In the inventive process, the mixture of a separation layer forming high molecular weight compound and inorganic fine particles is introduced into the cylinder block of the homogenizer by suction, compressed by forward movement of the plunger, thrust into a small gap between the valve sheet and valve member and then ejected into a low pressure cavity at a high speed.

In these steps, shearing action caused by cavitation and pulverizing action caused by impact are applied to the mixture which is further made into ultra-fine particles to form a dispersion.

The resulting dispersion is recycled into the cylinder block of the homogenizer to repeat the dispersion treatment, thereby obtaining a dispersion in which the ultra-fine particles are stably dispersed.

Also, the homogenizer used in the inventive process can perform the dispersion treatment under such conditions that the mixture shows a viscosity of 10,000 centipoises or less, by heating the mixture, so that the resulting blood separating agent can be packed and shipped in a drum vessel maintaining the low viscosity.

In addition, a uniform blood separating agent can be produced when an organic gelling agent is used.

Other objects and advantages of the present invention will be made apparent as the description progresses.

BRIEF DESCRIPTION OF THE DRAWINGS

In these drawings, "A" indicates a mixer, "1" indicates a homogenizer, "2" indicates a cylinder block, "7"indicates a valve body, "8" indicates a valve sheet, "9" indicates a valve member, "5" indicates a plunger, "23" indicates a heating mechanism, "s" indicates a small gap, "c" indicates a low pressure cavity, "14" indicates a tank and "22" indicates an exhaust tube.

DETAILED DESCRIPTION OF THE INVENTION (1) Blood separating agent:

The blood separating agent comprises (a) a separation layer-forming high molecular weight compound as the main component and (b) a thixotropy-providing agent such as inorganic fine particles or an organic gelling agent.

(2) Separation layer forming high molecular weight compound (a):

Various compounds ranging from low viscosity organic solvents and plasticizers to high viscosity high molecular weight oily materials can be used as the separation layer forming high molecular weight compound, provided that they have an intermediate specific gravity between those of the serum portion and clot portion or of the plasma portion and hematocyte portion. Practically, a high molecular weight oily substance having a viscosity of 20,000 to 600,000 centipoises (cps), preferably 30,000 to 100,000 cps, at a temperature of 25° C. is desirable from the viewpoint of its being able to give stable and appropriate fluidity and gelling properties.

Illustrative examples include those which have been described in the aforementioned patents, such as silicone, chlorinated polybutene, chlorinated polybutadiene, poly (meth)acrylate, polyisobutene, an α-olefin polymer, polystyrene, a copolymer of α-olefin or styrene with a dialkyl maleate, and the like. These may be used alone or as mixtures of two or more thereof.

Most preferred among these compounds is a copolymer comprised of 1 mol of α-olefin having 6 to 20, preferably 8 to 14, carbon atoms and 1 to 1.4 mols of a dialkyl maleate (the alkyl group may have 1 to 4, preferably 1, carbon atoms), having a viscosity of 40,000 to 100,000 centipoises at 25° C.

(3) Thixotropy providing agent (b):

As the thixotropy providing agent, the inorganic fine particles, organic gelling agents and the like described in the aforementioned patents can be used. Illustrative examples include inorganic fine particles such as those of hydrophobic silica (particularly colloidal silica), aliphatic amine derivatives of smectite clay and the like; and organic gelling agents such as glutamic acid amide, hydrogenated castor oil, dibenzylidene sorbitol and the like. These may be used alone or as mixtures of two or more thereof.

The thixotropy providing agent (b) may be used in an amount of from 0.5 to 5 weight parts as the inorganic fine particles or from 0.1 to 1 weight part as the organic gelling agent based on 100 weight parts of the separation layer forming high molecular weight compound (a).

(4) Optional components:

In addition to the aforementioned components (a) and (b), titanium oxide, alumina, polyethylene particles, polystyrene particles, and the like, may be blended in an amount of from 0 to 20 weight parts based on 100 weight parts of the component (a).

Figure 1:
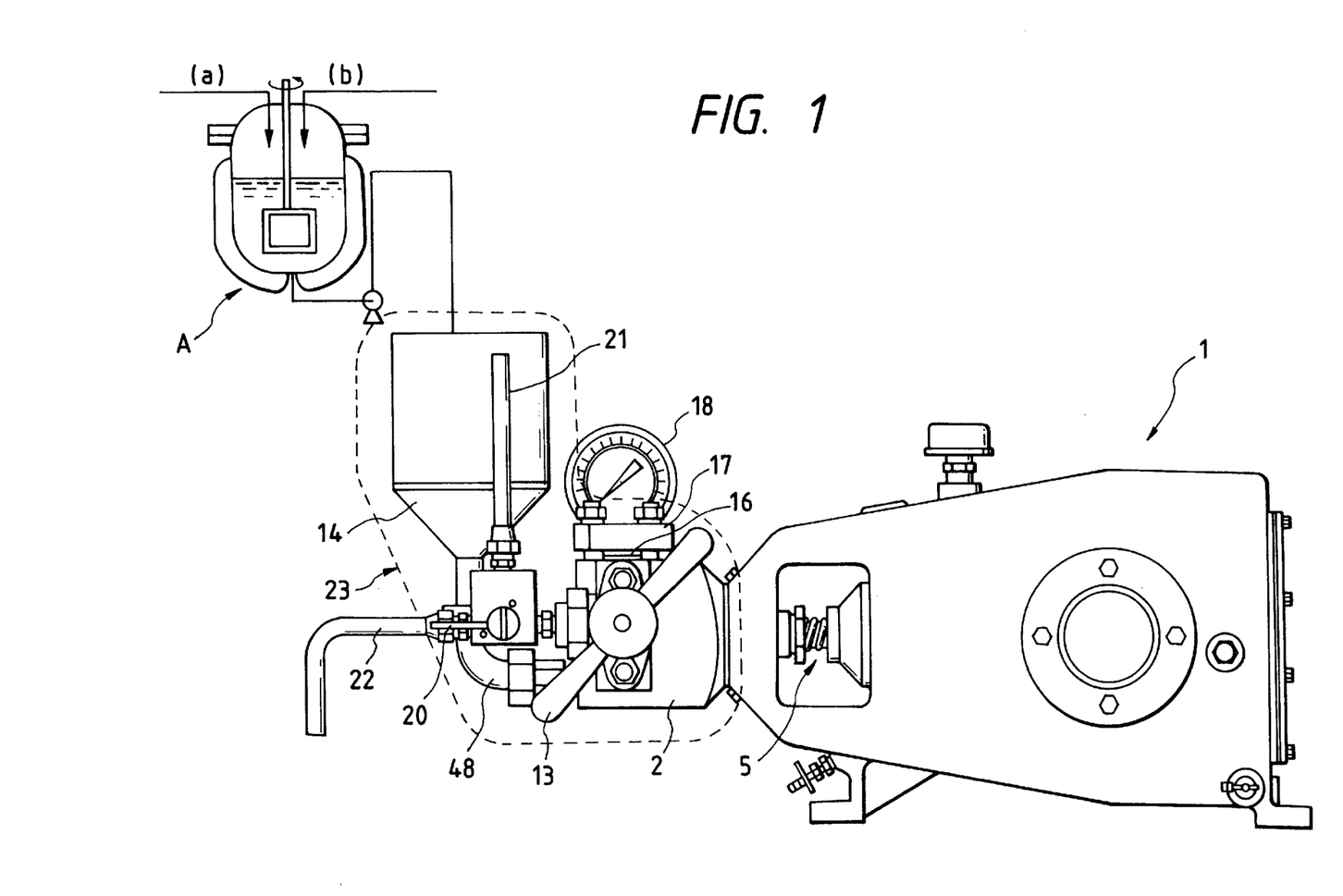
FIG. 1 is an illustration showing an example of the process for carrying out the present invention and a schematic view of a device to be used therein.
Figure 2:
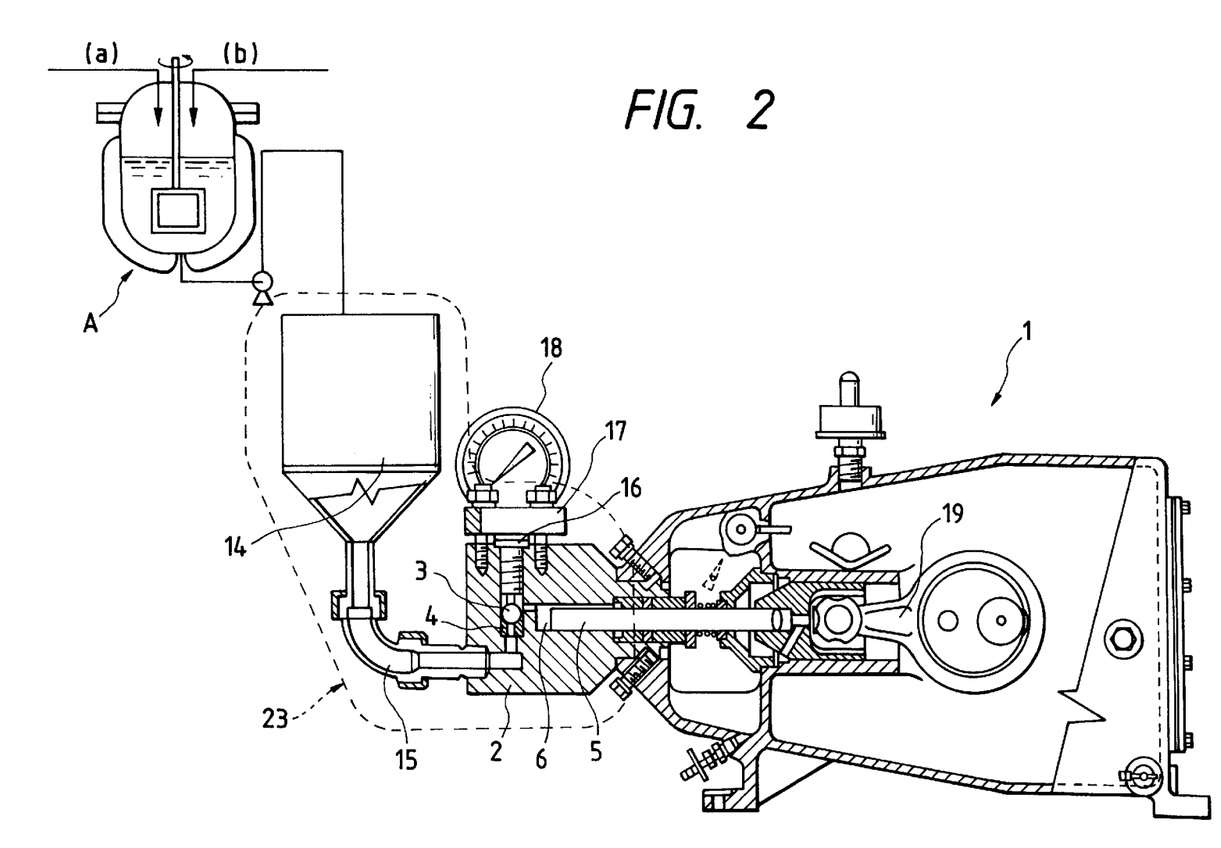
FIG. 2 is an illustration showing a rear elevation of the homogenizer.

(5) Preparation of mixture solution:

The separation layer forming high molecular weight compound (a) and thixotropy providing agent (b) are mixed by stirring in mixer (A) shown in FIGS. 1 and 2, which is equipped with a mixing blade in the form of a paddle, propeller, horseshoe, ribbon, lattice, Max-blend, Full zone or the like type.

As occasion demands, the mixture may be heated at a temperature of from 40° to 200° C., preferably from 60° to 160° C., to facilitate the stirring. The stirring may be carried out for 0.1 to 2 hours.

By this treatment, the mixture becomes a dispersion having a particle size of from 0.01 to 8 μm or a uniform solution (when an organic gelling agent is used).

Preparation of the mixture may also be carried out by the joint use of two or more mixers. For example, a vertical type mixer equipped with a lattice type mixing blade may be used jointly with a mixer, or a vertical type mixer equipped with a propeller mixing blade may be used jointly with a twin screw extruder having paddle and screw means.

The thus prepared mixture solution is transferred into the storage tank (14) of homogenizer (1) with the aid of a pump.

(6) Homogenizer (1)

The homogenizer to be used in the present invention is a homogenizer having a cylinder block equipped with a plunger capable of performing reciprocating movement and a valve body which is connected thereto and equipped with a valve member, a valve sheet and an impact ring.

The following describes an example of the homogenizer with reference to the drawings.

Figure 3:
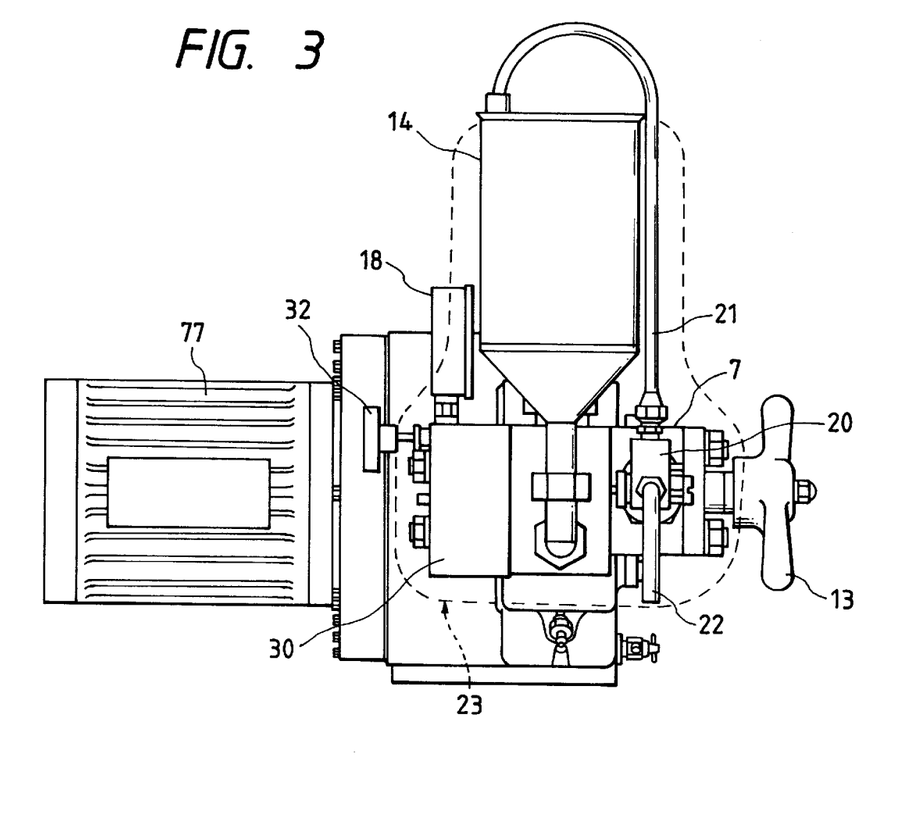
FIG. 3 is an illustration showing a side elevation of the homogenizer.
Figure 4:
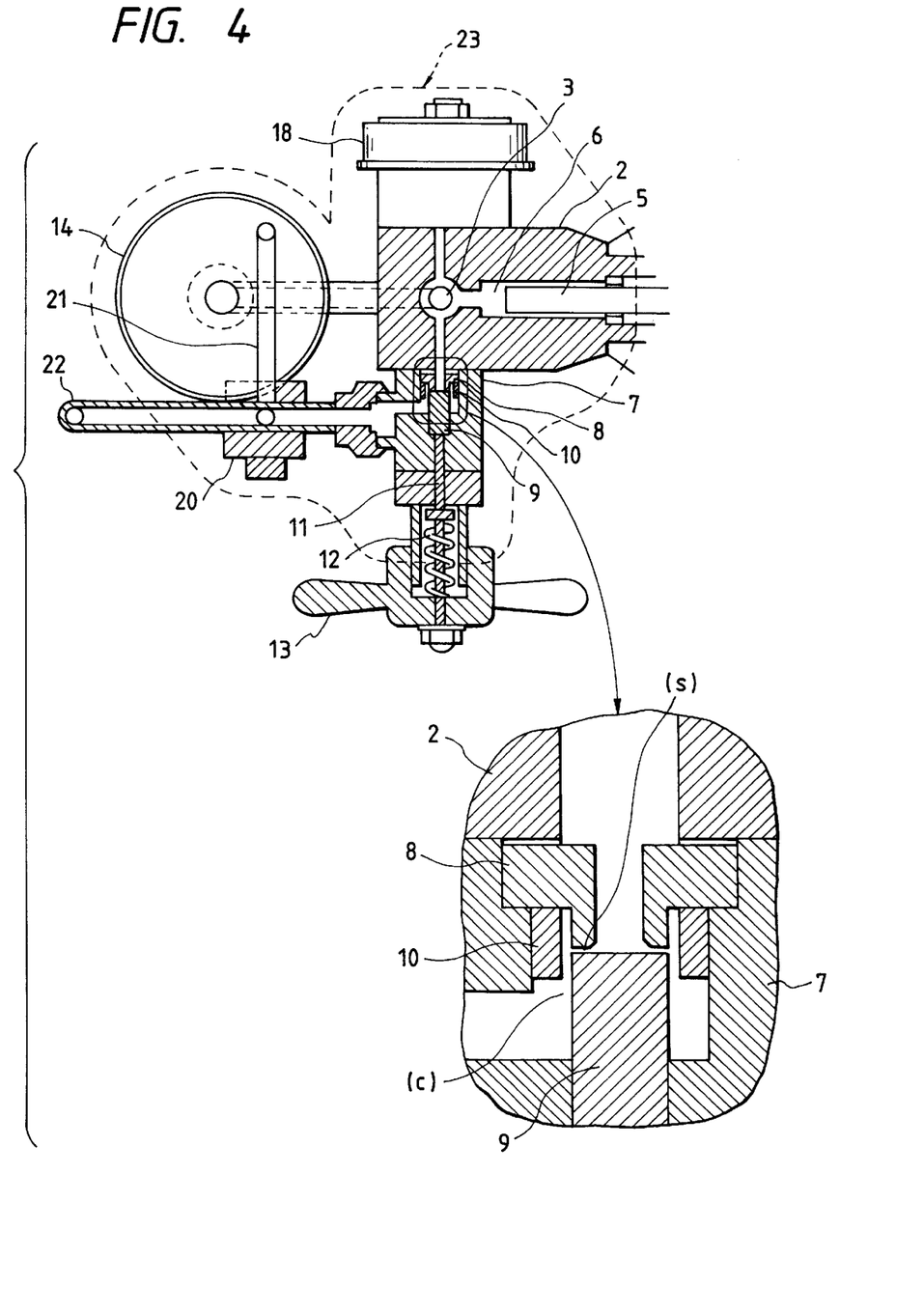
FIG. 4 is an illustration showing a greatly enlarged horizontal sectional view of the cylinder block and valve body and a further enlarged view of parts thereof.

FIG. 1 is an elevational view of the homogenizer, FIG. 2 is a fragmentary elevational view of the homogenizer, FIG. 3 is a side elevation view of the homogenizer and FIG. 4 is an illustration showing a greatly enlarged horizontal sectional view of the cylinder block part and valve body and a further enlarged view of parts thereof.

According to FIGS. 1 to 4, homogenizer (1) has a pump ball valve (3), a pump valve sheet (4), a plunger (5), a valve body (7) connected to a cylinder block (2), a valve sheet (8), a valve member (9) and an impact ring (10) for use in dispersion treatment, a valve rod (11), a valve spring (12) and a handle (13) for use in the adjustment of loading pressure, a storage tank (14) of the mixture, a feed tube (15), an upper cap plug (16) arranged in the cylinder block, an upper cap (17) which holds the plug, a pressure gage (18) for use in the measurement of liquid pressure inside the cylinder block, a plunger driving means (19) which enables reciprocating movement of the plunger, a switch cock (20) connected to the valve body, a recycle tube (21) and a discharge tube (22). In the drawings, "s" is a small gap arranged between the valve sheet and valve member.

A plunger having such cylinder block and valve body is available from APV Gaulin under trade names of Homogenizer "M-Series", "MS-Series" and "MC-Series" and from Izumi Food Machinery as HU-A, HU-C and HU-H.

Since these homogenizers are not equipped with a heating mechanism for the cylinder block, valve body and the like, a steam-circulating copper tube is coiled around these parts to be used as a heating mechanism (23) as shown in FIGS. 1 and 3 with a dotted line.

This heating mechanism may also be provided using an electric heater or a steam jacket.

(7) Preparation of blood separating agent

The mixture supplied in a predetermined amount into tank (14) of homogenizer (1) from the mixer (A) is introduced into cylinder (6) by the rearward movement of plunger (5), via feeding tube (15) and passing through the central passage of pump valve sheet (4) of cylinder block (2).

Next, the mixture compressed by the forward movement of plunger (5) is forced into a small gap (s) between valve member (9) and valve sheet (8), where a loading pressure is set to a predetermined level by tightening valve spring (12) of valve rod (11) with handle (13), and ejected into low pressure part (C) at a high speed. By this treatment, particles are sheared by cavitation and smashed into the inner wall of impact ring (10) to receive pulverization action by the impact, so that the mixture solution becomes a dispersion of 0.01 to 8 μm in particle size or a uniform gel. In this case, when viscosity of the mixture is adjusted to 10,000 centipoises or less by heating, pump ball valve (3) acts normally so that stable operation can be achieved. Because of this, cylinder block (2) and its accompanying parts are heated to 60° to 160° C., preferably 80° to 140° C., with a heater, a steam jacket or a steam trace. The thus treated solution discharged from low pressure cavity (C) of valve body (7) is passed through switch cock (20) and returned to tank (14) via recycle tube (21) and then into the cylinder block of homogenizer to be treated again. By this recycle dispersion treatment, the mixture becomes a stable dispersion. When the recycle is repeated a predetermined number of times, the load is released with valve member (9) to discontinue the operation, switch cock (20) is switched and then the operation is started again under no load to pack the product in a container through discharge tube (22).

Viscosity of the thus discharged blood separating agent becomes high as the temperature lowers and reaches 200,000 to 800,000 centipoises at 25° C.

Since the blood separating agent should have an intermediate specific gravity between those of the serum portion and clot portion or of the plasma portion and hematocyte portion, it is desirable that its specific gravity at 25° C. is within the range of from 1.028 to 1.060. For example, in the case of a blood separation tube in which the blood separating agent is placed on its bottom, a larger difference between the specific gravity of the clot or hematocyte component and that of the blood separating agent is desirable, because the ability of the separating agent to float becomes large during centrifugation. However, a specific gravity of less than 1.028 is not desirable, because a portion of the separating agent having a small specific gravity will be separated into the serum or plasma component after centrifugation.

The thus obtained blood separating agent is light yellow, transparent, odorless and particularly inert to blood. In other words, it does not cause adsorption, elution, and the like, of blood, contains no volatile components and is stable for an extended period of time. Also, being low in polarity, its adsorption to and solubility in drugs contained in sera are low, so that it does not exert a negative influence upon the measured values of drugs and more accurate test data can therefore be obtained. In using the blood separating agent of the present invention, it is customary to store it in the bottom portion of a vacuum type or non-vacuum type blood-collecting tube in advance.

EXAMPLES

Examples of the present invention are given below by way of illustration and not by way of limitation. Preparation of mixture:

Example 1

An agitation vessel is charged with 100 weight parts of a copolymer comprised of 1 mol of a mixture of α-olefins having 12 and 14 carbon atoms and 1.3 mols of dimethyl maleate (manufactured by Mitsubishi Chemical; about 60,000 centipoise in viscosity and 1.033 in specific gravity at 25° C.) which was subsequently heated to 100° C. in an oil bath while stirring with a conventional agitator at 700 rpm. Thereafter, this was mixed with 2 weight parts of an aliphatic amine derivative of smectite clay (trade name, "Benton 38"; manufactured by NL Industry) and 1 weight part of colloidal silica (trade name, "Aerosil R972"; manufactured by Japan Aerosil) and stirred for about 1 hour at the same temperature to obtain a uniform mixture solution.

(Inventive Example 1)

Using a pump, a 0.6 liter portion of the 100° C. mixture solution obtained in Example 1 was fed into a tank of the APV Gaulin Laboratory Homogenizer shown in FIGS. 1 to 4 (manufactured by APV Gaulin; type, 15MR-8TA; width, 920 mm; depth, 640 mm; height, 540 mm; treating capacity, 57 liters per hour; motor, 2.2 KW, 200 V).

The cylinder block and its appending parts of the homogenizer were kept at a temperature of 100° to 105° C. by steam trace heating.

The valve member was set to a no-load condition, and the switch cock was set to the recycle tube side to operate the homogenizer and circulate the mixture in the tank.

Using the handle, loading pressure of the valve member was increased to 300 kg/cm$^2$, and the operation was carried out under this condition for 7 minutes (corresponding to 11 cycles). Thereafter, the operation was discontinued by releasing the load on the valve member and then the operation was started again under a no-load condition by setting the switch cock to the discharge tube side to recover the thus dispersion-treated mixture (blood separating agent) in a container. Viscosity of the blood separating agent was about 400,000 centipoise at 25° C.

Figure 5:
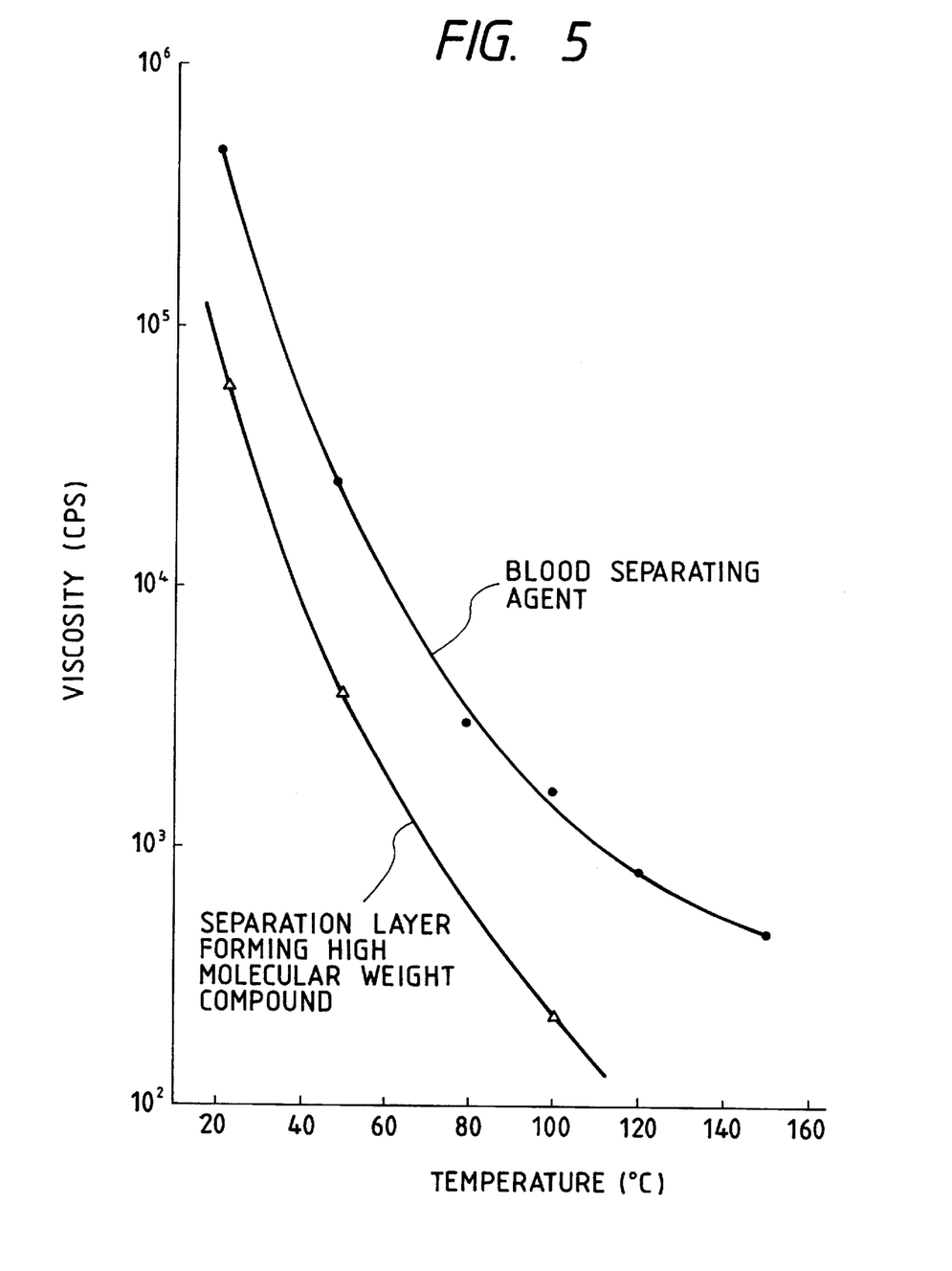
FIG. 5 is a graph showing a relationship between viscosity of a separation layer forming high molecular weight compound or a blood separating agent and temperature.

FIG. 5 shows the relationship between viscosity and temperature of the copolymer of α-olefin having 12 to 14 carbon atoms and dimethyl maleate and of the blood separating agent.

Flow length of laid gel, i.e. gel laid horizontally, (average of 10 gels) of the blood separating agent (specific gravity, 1.045) at room temperature or 50° C. was measured on the first day of laying the gel horizontally and one week thereafter by the following method. The results are shown in Table 1.

Measuring method

Figure 6:
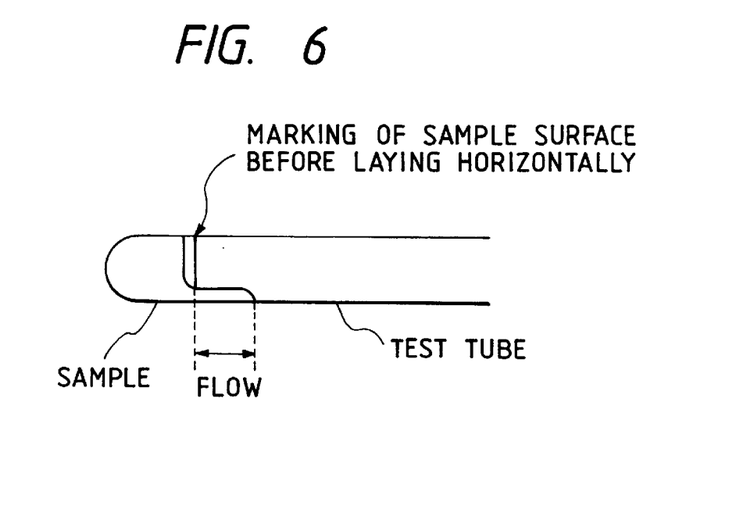
FIG. 6 is an illustration showing a method for measuring gel flow of the blood separating agent.

The blood separating agent is dispensed in 1.7 g portions into 10 cc capacity test tubes (manufactured by Terumo; trade name, VP-P100 "Venoject Vacuum Blood Collecting Tube"), taking such care that it does not adhere to the inner wall of the tubes. Next, the tubes are subjected to 10 minutes of centrifugation at 1,600 G. After 1 day of standing in a vertical position at 25° C., the resulting tubes are laid horizontally and stored at 25° or 50° C. to measure flowed length of the gel one day and one week thereafter. The measuring method is shown in FIG. 6.

(Comparative Example 1)

A 0.6 liter portion of the mixture solution obtained in Example 1 was subjected to two pass dispersion treatment using a three-roller mill manufactured by Buhler (type, SDH-300/150; width, 1,130 mm; depth, 620 mm; height, 1,050 mm; roller size, 150 mm in diameter and 300 mm in length; motor, 2.2 KW, 200 V) to produce a blood separating agent.

In this case, total operation time of the two-pass treatment was 1 hour. Flow length of laid gel of this blood separating agent is shown in Table 1.

(Inventive Example 2)

A mixture was obtained by adding 0.25 weight parts of an organic gelling agent dibenzylidene sorbitol, to 100 weight parts of the α-olefin/dimethyl maleate copolymer used in Inventive Example 1, stirring the mixture for 1 hour at 140° C. and then spontaneously cooling the product.

A 0.6 liter portion of the thus obtained mixture was fed into the homogenizer used in Inventive Example 1 and treated at 80° C. for 7 minutes under a pressure of 300 kg/cm$^2$ to obtain a uniform blood separating agent (specific gravity, 1.045). Flow length of laid gel of this blood separating agent is shown in Table 1.

Serum separation test:

About 1.5 g of each of the blood separating agents produced in Inventive Example 1, Comparative Example 1 and Inventive Example 2 were placed on the bottom of a 10 cc capacity blood collecting tube, and a whole blood sample was introduced into the resulting tube and allowed to stand. When the sample was separated into serum and clot portions with the progress of blood coagulation, the tube was subjected to 10 minutes of centrifugation at 3,000 rpm to find that a gel layer of each of the blood separating agents was formed between the serum and clot portions. The serum was able to be easily removed from the blood collecting tube by decantation.

TABLE 1

|  | Inventive Example 1 | Comparative Example 1 | Inventive Example 2 |
| --- | --- | --- | --- |
| Apparatus | valve homogenizer | three roller system | valve homogenizer |
| Thixotropy providing agent | inorganic fine particles | inorganic fine particles | organic gelling agent |
| Time for 0.6 liter Blood separating agent | 7 minutes | 60 minutes | 7 minutes |
| Specific gravity | 1.045 | 1.045 | 1.045 |
| Viscosity (cps/25° C.) | ca. 400,000 | ca. 400,000 | ca. 600,000 |
| Flow of laid gel |  |  |  |

TABLE 1-continued

|  | Inventive Example 1 | Comparative Example 1 | Inventive Example 2 |
| --- | --- | --- | --- |
| 25° C., mm/day | 1.0 | 1.1 | 0.3 |
| 25° C., mm/week | 1.3 | 1.4 | 0.5 |
| 50° C., mm/day | 2.5 | 2.7 | 1.5 |
| 50° C., mm/week | 4.7 | 4.7 | 3.3 |

Thus, according to the process of the present invention, a blood separating agent capable of showing almost the same performance of the prior art counterparts can be obtained with a productivity per unit time which is 8 times or more higher than those of the conventional processes, without causing contamination by dust and dirt.

What is claimed is:

1. A process for producing a blood separating agent, which comprises:

supplying a mixture containing (a) a separation layer forming high molecular weight compound as a main component and (b) a thixotropy-providing agent selected from the group consisting of inorganic fine particles and organic gelling agents into a cylinder block of a homogenizer, wherein the homogenizer comprises (i) the cylinder block equipped with a plunger capable of performing reciprocating movement and (ii) a valve body which is connected to the cylinder block and equipped with a valve member, a valve sheet and an impact ring; and applying a compressive shearing stress to the mixture in the homogenizer by forward movement of the plunger to force the mixture through a gap between the valve member and valve sheet, at such a temperature that viscosity of the mixture becomes $1\times10^4$ centipoises or less, thereby obtaining a blood separating agent in the form of a dispersion or a uniform gel;

wherein the homogenizer further comprises a heating element for heating both of the cylinder block and the valve body.

2. The process for producing a blood separating agent according to claim 1, wherein the compressive shearing stress is applied to the mixture in the homogenizer at 60° to 160° C.

3. The process for producing a blood separating agent according to claim 2, wherein the mixture to be supplied into the homogenizer has a temperature of from 60° to 160° C.

4. The process for producing a blood separating agent according to claim 1, wherein 0.5 to 5 weight parts of the inorganic particles or 0.1 to 1 weight part of the organic gelling agent is blended as component (b) with 100 weight parts of component (a).

5. The process for producing a blood separating agent according to claim 1, wherein said heating element comprises a steam-circulating tube coiled around the cylinder block and the valve body.

6. The process for producing a blood separating agent according to claim 1, wherein said heating element comprises an electric heater or a steam jacket for transferring heat to the cylinder block and the valve body.

7. The process for producing a blood separating agent according to claim 1, wherein the separation layer forming high molecular weight compound (a) is a copolymer of α-olefin having 6 to 20 carbon atoms with a dialkyl maleate, wherein an alkyl group of the dialkyl maleate has 1 to 4 carbon atoms; and the thixotropy providing agent (b) is selected from the group consisting of colloidal silica and clay.

8. A process for producing a blood separating agent, which comprises:

supplying a mixture containing (a) a separation layer forming high molecular weight compound as a main component and (b) a thixotropy-providing agent selected from the group consisting of inorganic fine particles and organic gelling agents into a cylinder block of a homogenizer, wherein the homogenizer comprises (i) the cylinder block equipped with a plunger capable of performing reciprocating movement and (ii) a valve body which is connected to the cylinder block and equipped with a valve member, a valve sheet and an impact ring; and applying a compressive shearing stress to the mixture in the homogenizer by forward movement of the plunger to force the mixture through a gap between the valve member and valve sheet, at such a temperature that viscosity of the mixture becomes $1 \times 10^4$ centipoises or less, thereby obtaining a blood separating agent in the form of a dispersion or uniform gel;

wherein the separation layer forming high molecular weight compound (a) is a copolymer of α-olefin having 6 to 20 carbon atoms with a dialkyl maleate, wherein an alkyl group of the dialkyl maleate has 1 to 4 carbon atoms; and the thixotropy providing agent (b) is selected from the group consisting of colloidal silica and clay.

* * * * *